US011318118B1

United States Patent
Karmali

(10) Patent No.: US 11,318,118 B1
(45) Date of Patent: May 3, 2022

(54) METHODS AND COMPOSITIONS FOR TREATING SARS-COV-2 INFECTION USING CARBOXYAMIDOTRIAZOLE OROTATE

(71) Applicant: Rashida A. Karmali, Brooklyn, NY (US)

(72) Inventor: Rashida A. Karmali, Brooklyn, NY (US)

(73) Assignee: TACTICAL THERAPEUTICS INC., New York, NY (US)

( * ) Notice: Subject to any disclaimer, the term of this patent is extended or adjusted under 35 U.S.C. 154(b) by 23 days.

(21) Appl. No.: 17/301,493

(22) Filed: Apr. 5, 2021

(51) Int. Cl.
  A61K 31/505 (2006.01)
  A61P 31/14 (2006.01)
  A61K 31/4192 (2006.01)
  A61K 45/06 (2006.01)

(52) U.S. Cl.
  CPC .......... *A61K 31/4192* (2013.01); *A61K 45/06* (2013.01); *A61P 31/14* (2018.01)

(58) Field of Classification Search
  CPC .............................. A61K 31/505; A61P 31/14
  USPC ........................................................ 514/274
  See application file for complete search history.

(56) References Cited

U.S. PATENT DOCUMENTS 7,973,013 B2  7/2011  Cho et al.
8,912,223 B2  12/2014  Karmali

OTHER PUBLICATIONS

Korber B, et al, Tracking changes in SARS-CoV-2 Spike: evidence that D614 increases Infectivity of the COVID-19 virus, Jun. 2020, Cell doi.org/10.1016/cell 2020.06.043.
Guo L et al. Carboxyamidotriazole ameliorates experimenta colitis by inhibition of cytokine production, nuclear factor kappaB . . . 2012, J Pharmacol Exp Ther 342: 356-65.
Bauer KS et al. Carboxyamidotriazole inhibits angiogenesis by blocking the calcium-mediated nitric oxide synthase vascular . . . 2000, J.Pharmacol Exp Ther 292: 31-37.
Alllesandro R, et al Effects of carboxyamidotriazole on in vitro models of imatinib-resistant chronic . . . 2008, J Cell Physiol 215: 111-121.
Omuro A et al Multicenter Phase IB Trial of Carboxyamidotriazole orotate (CTO) and Temozolomide . . . 2018, J. Clin Oncol 36: 1702-1709.
Ge S et al Carboxyamidotriazole induces apoptosis in bovine endothelial and human glioma cells 2000, Clin Cancer Res 6: 1248-54.
Kohn E et al In vivo efficacy of a novel inhibitor of selected signal transduction pathways including calcium . . . 1992, 52: 3208-3212.
Broder et al. 2016, Nature Microbiology 2: 16184.
Balasubramantam m. 2020 COVID-19 : It is time to revisit the research on callcium channel drug targets? Jun. 2020, EMJ Diabet .Doi:10335901 emjdiab/200608.
Chang-Graham AL et al RotavirusCalcium Dysregulation Manifests as dynamic calcium signaling in the cytoplasm and . . . 2019, Science Reports 9: 10822.
Fujioka Y et al A sialylated voltage-dependent Ca2+ channel binds hemagglutinin and mediates Influenza A virus entry . . . ,2018 Cell Host & Microbe 23: 809-818.
Bai D et al Porcine deltacoronavirus (PDCoV) modulates calcium influx to favor viral replication, 2020, Virology 539: 38-48.
Bouhaddou M et al The Global phosphorylation laandscape of SARS-CoV-2 infection. 2020, Cell 11493 https://doi.org/10.1016/cell.2020.06.034.
Moore JB et al Cytokine release syndrome in severe COVID-19, 2020, Science 368: 473-4.
Kohn EC et al Angiogenesis: role of calcium-mediated signal transduction, 19995, Proc Natl Acad Sci 92: 1307-11.
Yasui H et al Selective Inhibition of mitogen induced transactivation of the HIV long terminal repeat by carboxyamidotriazole . Calcium . . . 1997, JBiol Chem 272: 28762-28770.
Ogando NS, et al, SARS-coronavirus-2 replication in Vero E6 cells: replication kinetics, rapid adaptation and cytopathology, bioRxiv preprint doi: https://doi.org/10.1101/2020.04.20.049924, Apr. 2020.

*Primary Examiner* — Raymond J Henley, III
(74) *Attorney, Agent, or Firm* — Rashida A. Karmali, Esq.

(57) ABSTRACT

This invention provides compositions and methods for treatment of mild, moderate and severe stages of SARS-CoV-2 infection, particularly COVID-19 disease caused by wild type and mutant strains of SARS-CoV-2 using 5-amino-1-(4-(4-chlorobenzyl)-1, 2, 3-triazole-4-carboxamide orotate. Carboxyamidotriazole orotate (CTO) alone or in combination with other therapeutics in standard of clinical care are useful for directing antiviral effects and host-directed antiviral effects against wild type and mutant strains of SARS-CoV-2 throughout the viral life cycle.

8 Claims, 2 Drawing Sheets

Figure 1:
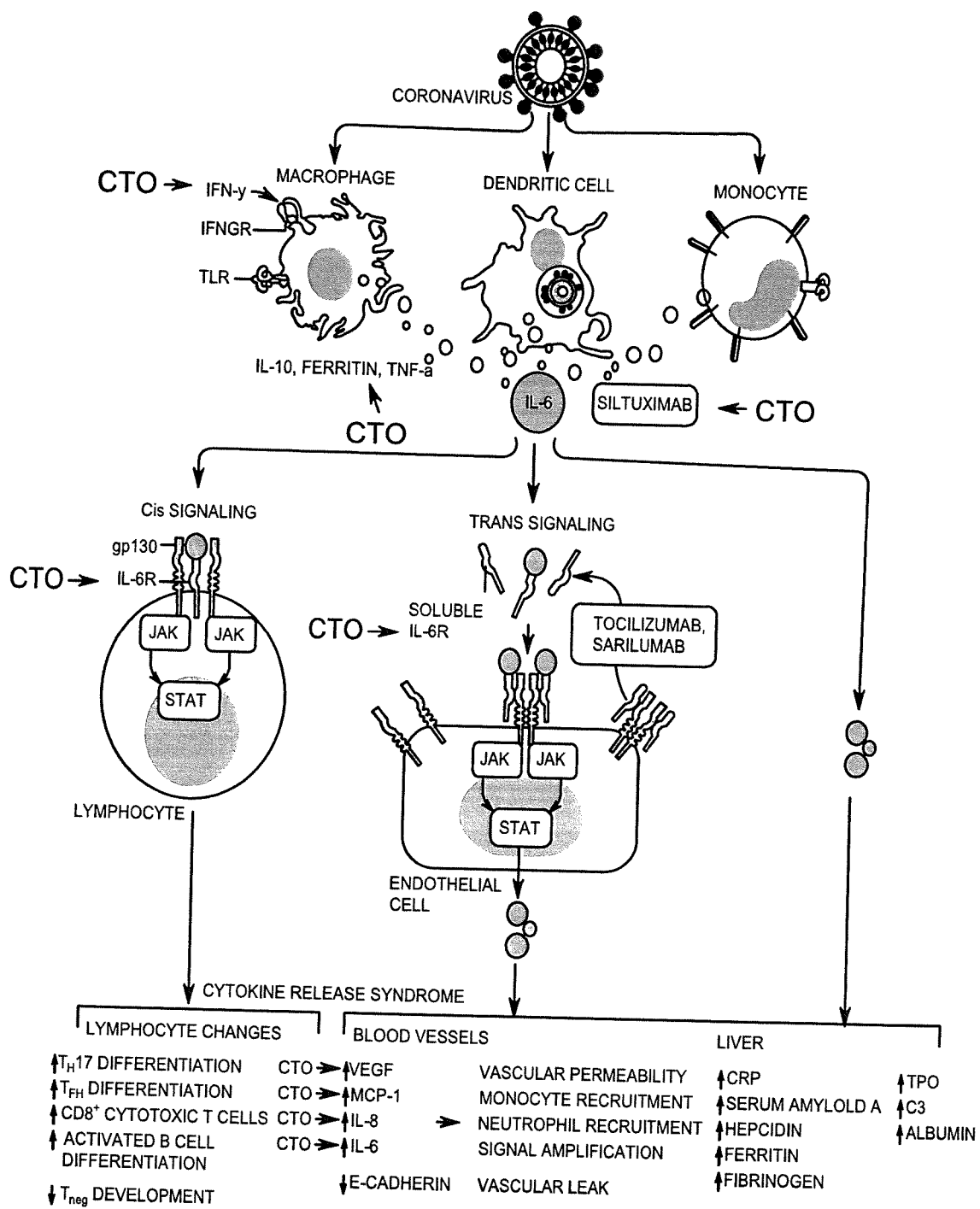

METHODS AND COMPOSITIONS FOR TREATING SARS-COV-2 INFECTION USING CARBOXYAMIDOTRIAZOLE OROTATE

CROSS-REFERENCE TO OTHER APPLICATION

This application is a Divisional of U.S. patent application Ser. No. 16/985,789 filed on Aug. 5, 2020, which is incorporated herein, with references in its entirely.

1. FIELD OF INVENTION

This invention provides compositions and methods for treatment of mild, moderate and severe stages of SARS-CoV-2 infection, particularly COVID-19 disease caused by wild type and mutant strains of SARS-CoV-2 using 5-amino-1-(4-(4-chlorobenzyl)-1, 2, 3-triazole-4-carboxamide orotate. Carboxyamidotriazole orotate (CTO) alone or in combination with other therapeutics in standard of clinical care are useful for directing antiviral effects and host-directed antiviral effects caused by wild type and mutant strains of SARS-CoV-2 throughout the viral life cycle. Specifically, the methods and compositions of CTO of this invention are directed to inhibit the SARS-CoV-2 induced cytokine release, cytokine syndrome and cytokine storm and associated damage by inhibiting the calcium signals required by cells of the immune system, for example macrophages, dendrites, monocytes, T-cells, B-cell and blood vessel endothelial cells. This invention is based on unexpected and very important effects of CTO directed to inhibiting phosphorylation of host and viral proteins caused by SARS-CoV-2 infection and inhibition of viral replication. More specifically the invention relates to methods and compositions of CTO to inhibit calcium signaling extra-cellularly and intracellularly to inhibit viral entry inside the host cell, and further to inhibit replication and transcription to produce viral RNA replication and virons which are released from the cell via a non-lytic mechanism. This invention is directed to preventing virus particles and structural proteins from suppressing the innate immune responses by macrophages, dendritic cells, T-cells and B-cells. This invention is also directed to methods and compositions of CTO to inhibit the development of excessive adaptive immune responses resulting in pro-inflammatory cytokines (referred to as "cytokine storm") that contribute to lung injury, edema, coagulation and disease progression to other organs and systems. The invention is further directed to increase some anti-inflammatory cytokines concurrently. Currently, there are few options left for approved treatment of SARS-CoV-2 at different inflection points except for early disease with antiviral remdesivir.

2. BACKGROUND TO THE INVENTION

The first cases of COVID-19 were reported from Wuhan, China in early December 2019, now known to be caused by the novel beta-coronavirus, named as Severe acute respiratory syndrome coronavirus 2 (SARS-CoV-2). Within a span of months, COVID-19 has become pandemic due to its transmissibility, spreading across continents with the number of cases and deaths rising daily. Although most infected individuals exhibit a mild illness (80%), 14% have serious and 5% have critical illness. Approximately 10% require hospital admission due to COVID-19 pneumonia, of which approximately 10% require ICU care, including invasive ventilation due to acute respiratory distress syndrome (ARDS). While mortality appears to be more common in older individuals and those with comorbidities, such as chronic lung disease, cardiovascular disease, hypertension, diabetes and cancer, young people with no comorbidities also appear to be at risk for critical illness including multi-organ failure and death.

SARS-CoV-2, unlike related SARS-CoV, appears to be more efficient at human-to-human transmission, infecting approximately 2.5 people for every infected person. The high viral load in early phase of infection may account for the high transmissibility. SARS-CoV-2 infects mainly epithelial cells in the lung. The virus may enter macrophages, monocytes and dendritic cells and these cells may produce the pro-inflammatory cytokines such as IL-1β, IL-6, INF-γ and TNFα, which then distribute via systemic circulation, increasing blood flow and enabling leukocytes and plasma proteins to reach extravascular sites of injury. A failure to clear the virus early may result in an exaggerated and prolonged immune response which can manifest itself as a cytokine storm. Lung injury is a common consequence of a cytokine storm in the alveolar environment which can progress to acute respiratory distress syndrome (ARDS). These responses may compromise organ function when tissue edema causes a rise in extravascular pressures and a reduction in tissue perfusion.

Compensatory repair processes initiated after the onset of inflammation and healing occurs with fibrosis, which can result in permanent organ dysfunction. This process is similar to the way in which the immune system turns against the body in autoimmune diseases.

The time course from initial SARS-CoV-2 infection to an exaggerated and prolonged immune response is important to understand to plan therapies for intervention at different inflection points in disease progression.

For example, a vaccine would work at the very beginning to prevent infection. A vaccine and herd immunity are essential to recover from SARS-CoV-2 pandemic. Vaccines need to be tailored to the virus structure itself and government resources and regulatory authorities and the pharmaceutical industry have collectively embarked on developing vaccines expeditiously to prevent SARS-CoV-2 infections. Already, two Variants of SARS-CoV-22 have appeared—the D variant and the G variant (Korber et al, CellJune 2020, doi.org/10.1016/cell 2020.06.043)

Another approach taken is to use antibodies that bind to SARS-CoV-2 taken from individuals who have recovered from the infection and are willing to donate blood from which the antibodies are extracted and used to treat infected patients. The antibodies may be used in high-risk individuals to prevent infection or early in infection to present viral replication and spread thus providing passive immunotherapy.

An important category of therapies early in the disease is direct-acting antivirals that bind to viral proteins to inhibit function. Efforts to identify nucleotide analogues that inhibit SARS-CoV-2 RNA-dependent RNA polymerase (RdRp) have led to identification of several compounds from the library of nucleotide analogues. Efforts to test FDA-approved antivirals and evaluate them as potential therapeutics are underway. Remdesivir, a phosphoramidate prodrug containing 1'cyano modification on the sugar is converted in cells into an adenosine triphosphate analogue, which has been shown to inhibit SARS-CoV and SARS-CoV-2. It has now been approved as a therapeutic for emergency use.

Another category of potential therapeutic intervention comprises compounds with host directed anti-viral activity which disrupt the SARS-CoV-2 life cycle, for example inhibiting cell entry by acting as a decoy of angiotensinconverting enzyme 2 (ACE2) human receptor (e.g., hydroxycholoroquine). The viral structural S or spike protein facilitates viral entry into host target cells. The S protein has a conserved receptor binding domain and receptor binding motif that binds tightly to the ACE2 receptor. Priming of the S protein is then achieved by the action of the human type II transmembrane serine protease, resulting in fusion of viral and cellular membranes. Once inside the cell, the virus releases its RNA into the cytoplasm of the infected human cell, which undergoes translation to produce viral proteins required for subsequent viral RNA replication and transcription. Chloroquine and hydroxychloroquine have been used as anti-inflammatory agents in the treatment of autoimmune diseases such as arthritis and therefore, are being repurposed to prevent or treat early stages of SARS-CoV-2.

There are many unknowns about how the immune system fights SARS-CoV-2, but the innate and adaptive immune systems are important in clearing virus load in early stages of SARS-CoV-2 infection. However, in some infected individuals as disease progresses, there is an increase in inflammatory markers such as C reactive protein and pro-inflammatory cytokines—referred to as "cytokine storm" (Il-6, IL-8, TNFα and IL-1β), atrophy of the spleen and lymph nodes and reduced lymphocytes in lymphoid organs. Monocytes and macrophages predominate in the lungs with minimal lymphocyte infiltration and some patients exhibit T cell exhaustion. Numerous clinical trials of repurposed anti-inflammatory drugs targeting individual cytokines in the cytokine storm (IL-6R inhibitor tocilizumab, IL-6 inhibitor siltuximab, IL-1β inhibitor anakinra, IL-18 inhibitor Tadekinig alfa, IFN-γ inhibitor emapalumab and TNF-α inhibitor adalimumab) as well as less targeted therapies such as corticosteroids to dampen or inhibit the excessive adaptive response and to prevent a patient from progressing from moderate to severe disease requiring Intensive Care Unit care. Unfortunately, there is a legitimate concern and urgency that our health care system will be overtaken by patients requiring medical attention and hospitalization. Epidemiological models suggest that the pandemic will continue beyond the availability of a vaccine or the acquisition of herd immunity. Even if vaccines become available, expert virologists express concern that SARS-CoV-2 is mutating to different forms, for example two variants have been found D614 and G614.

Pharmacological interventions with repurposed existing therapeutics to intervene at key points in disease progression to down regulate the expression of proinflammatory cytokines with hydroxychloroquine or with specific anti-IL-6, anti-IL6R, anti-IL-1β, anti-IFN-γ or anti-TNFα are underway and listed on the website www.Clinicaltrials.gov. The effect of CAI (carboxyamidotriazole) was evaluated in preclinical models of acute and chronic inflammation including croton-oil induced ear edema, cotton-induced granuloma, rat adjuvant induced arthritis, acetic-acid induced writhing and formalin test. CAI inhibited vascular permeability stimulated by VEGF or histamine, decreased TNF-α and IL-1β at the site of inflammation and in serum supporting CAI is an anti-inflammatory and analgesic. (Guo, L et al, J. Pharmacol Exp Ther, 2008, 325:10-16). The effect of CAI was investigated in a preclinical model of inflammatory bowel disease. CAI inhibited colitis in animals as scored macroscopically and microscopically. CAI inhibited the production of TNF-α, IL-1β and IL-6 in serum, supernatant of peritoneal macrophages and lamina propria. CAI prevented NF-kB activation and inhibited NF-kB phosphorylation and degradation. CAI inhibited production of fibrinogenic cytokine transforming growth factor β and ameliorated the colitis and colonic fibrosis. (Guo, L et al, J. Pharmacol Exp Ther, 2012, 342:356-365). The effect of CAI was investigated in a preclinical model of inflammatory bowel disease. CAI inhibited colitis in animals as scored macroscopically and microscopically. CAI inhibited the production of TNF-α, IL-1β and IL-6 in serum, supernatant of peritoneal macrophages and lamina propria. CAI prevented NF-kB activation and inhibited NF-kB phosphorylation and degradation. CAI inhibited production of fibrinogenic cytokine transforming growth factor β and ameliorated the colitis and colonic fibrosis. (Guo, L et al, J. Pharmacol Exp Ther, 2012, 342:356-365) CTO is also being developed as an oncolytic drug against several solid cancers selected because it has demonstrated the ability to inhibit multiple kinase pathways in multiple types of targets e.g., PI3, AKT, PTEN, mTOR, RAS, RAF, MAPK, MEK, WnT/B-catenin, HDAC and HSP90. Bauer et al J Pharmacol Exp Ther. 292(1):31-7.2000; Alessandro et al, J Cell Physiol 215: 111-121,2008; Omuro, A. et al, J. Clin Oncology, 2018, 36: 1702-1709.

CTO is an orotate salt of CAI. CAI is an inhibitor of receptor-operated calcium channel-mediated calcium influx and is shown to have antiproliferative and anti-invasive functions in several human cancer cell lines, including human glioblastoma cells. By interrupting calcium mobilization as a second messenger, CAI can inhibit calcium-sensitive signal transduction pathways, including the release of arachidonic acid and its metabolites; nitric oxide release; the generation of inositol phosphates; and tyrosine phosphorylation (Ge et al, Clin Cancer Res 6: 1248-54, 2000; Kohn et al, Cancer Res 52: 3208-12,1992). CAI inhibits VEGF expression and secretion (Bauer et al, J Pharmacol Exp Ther 292: 31-7, 2000). CAI inhibits phosphorylation of cellular proteins STATS and CrkL, and induces apoptosis in imatinib mesylate-resistant chronic myeloid leukemia cells by down-regulating bcr-abl (Alessandro et al, J Cell Physio 215: 111-121, 2008). CTO inhibits Akt and Erk1/2 phosphorylation in exosomes stimulated HUVEC cell, targets the tumors and mechanisms that may induce drug resistance or interfere with the antitumor activity.

This invention is related to a novel method for treating severe acute respiratory syndrome coronavirus 2 (SARS-CoV-2) infection at different inflection points in SARS-CoV-2 infection and COVID-19 disease progression using carboxyamidotriazole orotate (CTO). Specifically, CTO is an orotate salt of carboxyamidotriazole (CAI). The structure of CAI does not act as a decoy for SARS-CoV-2 but instead, CAI is a first-in-class inhibitor of non-voltage calcium signaling at the cellular membrane level, extracellularly and intra-cellularly and controls the calcium stores in the endoplasmic reticulum and mitochondria. The present invention therefore unexpectedly provides a method to modulate calcium signaling that is critical to the expression of virulence of SARS-CoV-2 at every inflection point from infection to progression in the life cycle of the virus, to the production of different types of cytokines by cells of the immune system, to systemic coagulation, organ damage in heart, liver, kidneys and brain organoids.

The timing and duration of the CTO therapy may be determined to be from the start of SARS-CoV-2 infection at different stages in the disease progression. Based on the understanding of COVID-19 progression, CTO therapy can be administered orally during: 1) First stage when an infected individual shows no symptoms but is contagious from 5 days post-infection to 14 days, 2) Second stage when infected individual shows symptoms during 5 to 10 days and is contagious up to 21 days, 3) Third stage when infected individual shows severe symptoms from 8 to 20 days and is hospitalized while being contagious for 25 days, and Fourth stage of infected individual showing critical symptoms and is contagious throughout 8 to 21 days in Intensive Care Unit and death by 25 days.

According to the method of the invention, it is 1) necessary to identify an individual infected with the SARS-CoV-2 virus, 2) to record any symptoms and time, and 3) to select the most suitable CTO regimen alone or with a standard of care therapy if necessary to inhibit the calcium signaling in play during the life cycle of the SARS-CoV-2 infection. Thus, CTO provides a more effective and sustained therapeutic paradigm for successful control and treatment of SARS-CoV-2, a fundamental object of the invention.

3. SUMMARY OF THE INVENTION

The present invention seeks to meet an unmet need by using CTO alone or in combination with traditional standard of care (SOC) drugs in infectious diseases and viral infections to achieve successful treatment outcomes and improved survival. The combination therapy includes CTO to improve or maintain the antiviral activity of the vaccine or antiviral drug, to prevent the excessive production and release of several cytokines that are released after SARS-CoV-2 infection and to inhibit further disease progression.

The invention provides methods and compositions of CTO for maintaining antiviral activity directly against SARS-CoV-2, against host directed antiviral activity, immunomodulatory activity, anti-coagulation activity, and anti-organ damage activity in heart, kidney, liver, brain and other tissues.

Calcium signaling regulates a broad range of cellular processes including many viruses which modulate calcium signaling to favor their replication and pathogenesis. The role of calcium in infection by viruses such as SARS-CoV-2, SARS-CoV, MERS-CoV, etc is unknown.

The present invention provides a paradigm for the development of drug treatment regimens that are based on in vitro and in vivo preclinical and clinical studies of CTO to provide therapeutic activity against infection by viruses including but not limited by SARS-CoV-2, SARS-CoV or MERS-CoV, The present invention provides compositions of CTO as a therapeutic drug intervention with broad potential anti-viral and anti-inflammatory activity against SARS-CoV-2 and its variants in the treatment of COVID-19.

The present invention seeks to meet an unmet need by using CTO alone or in combination with traditional and new standard of care therapeutics to treat SARS-CoV-2 infection to achieve successful treatment outcomes and improved survival.

The invention also provides pharmaceutical compositions comprising an effective amount of CTO to improve the sensitivity of one or more companion drugs in SARS-CoV-2 infected cells, and to maintain a continuous inhibition of calcium signaling to inhibit the entry of the virus in host cells, to prevent and inhibit replication of the virus, to inhibit the conversion of the virus from acute to chronic phase, to prevent or reduce the development of resistance to either drug due to development of new viral mutations.

The invention provides methods and compositions for maintaining sensitivity of chemotherapeutic antiviral drugs and neutralizing antibodies by targeting host related antiviral activity with timely combination therapy with CTO.

The invention provides a paradigm for the development of drug treatment regimens that are based on preclinical and clinical studies to provide inflection points and targets to intervene and control the progression of SARS-CoV-2 in an infected individual not showing symptoms, in an infected individual showing mild/moderate symptoms, in an infected individual showing severe symptoms and in an infected individual showing critical symptoms. CTO will be administered by intranasal gastric tubing in patients on ventilators.

The invention provides a paradigm that designs a suitable combination regimen of CTO and an inhibitor of a specific cytokine selected from a list including VEGF, TNF-α, IL-6, IL-1β to inhibit the cytokine storm and related disease-causing factors.

The invention also provides pharmaceutical compositions comprising an effective amount of CTO to prevent or inhibit SARS-CoV-2 induced cytokine syndrome or cytokine storm and related damage due to inflammatory activities to the lung and all other parts of the body, administered in the range 50 mg/m$^2$ to 1500 mg/m$^2$ based on the patient's body surface.

The invention also provides pharmaceutical compositions comprising an effective amount of CTO to prevent or inhibit SARS-CoV-2 induced cytokine syndrome or cytokine storm and related damage due to inflammatory activities to the lung and all other parts of the body, administered as a fixed dose given daily and calculated based on quantity and type of factors causing the COVID-19 symptoms, for example cytokine levels and also the viral load and demographics of patients being treated.

It is the object of the invention to provide methods to design optimum compositions of one or more antiviral or pharmaceutical therapeutic in combination with CTO to increase the effectiveness of the drugs selected, to improve the treatment effects and to reduce the maladaptive immune response mounted by the patient to SARS-CoV-2. In other words, the invention provides a paradigm of achieving better efficacy, improving treatment effects over a prolonged period and improving the survival rates for different phenotypes of COVID-19 at early stage, moderate stage and severe stage.

Such an approach described above is based on unexpected findings when CTO was given to cancer patients who volunteered to participate in Phase I clinical studies of CTO to establish its safety and tolerability. Importantly, when plasma samples from patients were analyzed to measure different cytokines for three patients, it was found that compared with the baseline levels before administration of CTO that different doses of CTO reduced the levels of several cytokines measured during the forty-eight hours interval after taking the CTO.

This invention therefore provides an important, much needed and novel approach not only to obtain better efficacy using CTO in inhibiting few cytokines (VEGF, TNF-α, IL-6, IL-1β) that CAI was shown to inhibit in pre-clinical models, but also additional ones that are also increased in COVID-19 and implicated in the progression of the diseases by the rapid inflammatory damage caused to different organs and system universally. Additionally, CTO induced the increase of IFN-2α, IL-10 and IL-12p40. Table 1.

4. BRIEF DESCRIPTION OF FIGURES

FIG. 1 illustrates the key pathways to cytokine release as a result of SARS-Co-V2 infection leading to cytokine release syndrome and cytokine storm. Abbreviations used are: C3, complement 3; CRP, C reactive protein; IFN-g, interferon-g; IFNGR, IFN-g receptor; IL, interleukin; IL-6R, IL-6 receptor; JAK, Janus kinase; MCP-1, monocyte chemoattractant protein-1; STAT3, signal transducer and activator of transcription 3; TFH, T follicular helper cell; TH17, T helper 17 cell; TNF-α, tumor necrosis factor-α; TLR, Toll-like receptor; TPO, thrombopoietin; Treg, T regulatory cell; VEGF, vascular endothelial growth factor. Multiple targets for CTO are shown for IL-6, IL-6R, IL-8, TNF-α, IFN-γ, VEGF, MCP-1. Other CTO targets not shown are IL-1β, IL-1β, INF-2a.

Figure 2:
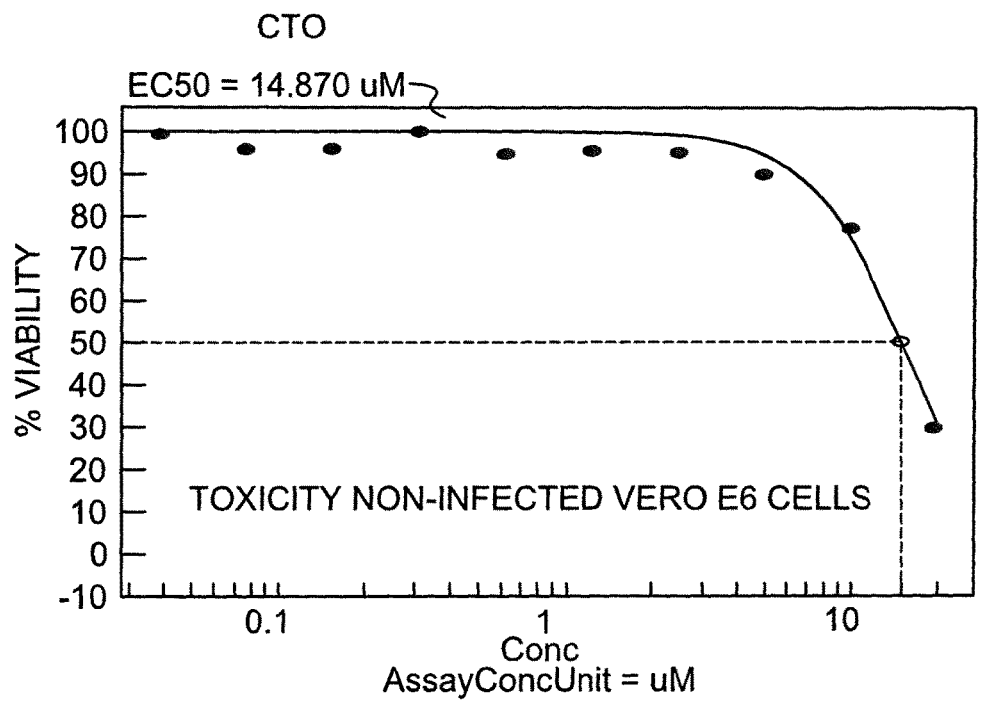
Figure 2:
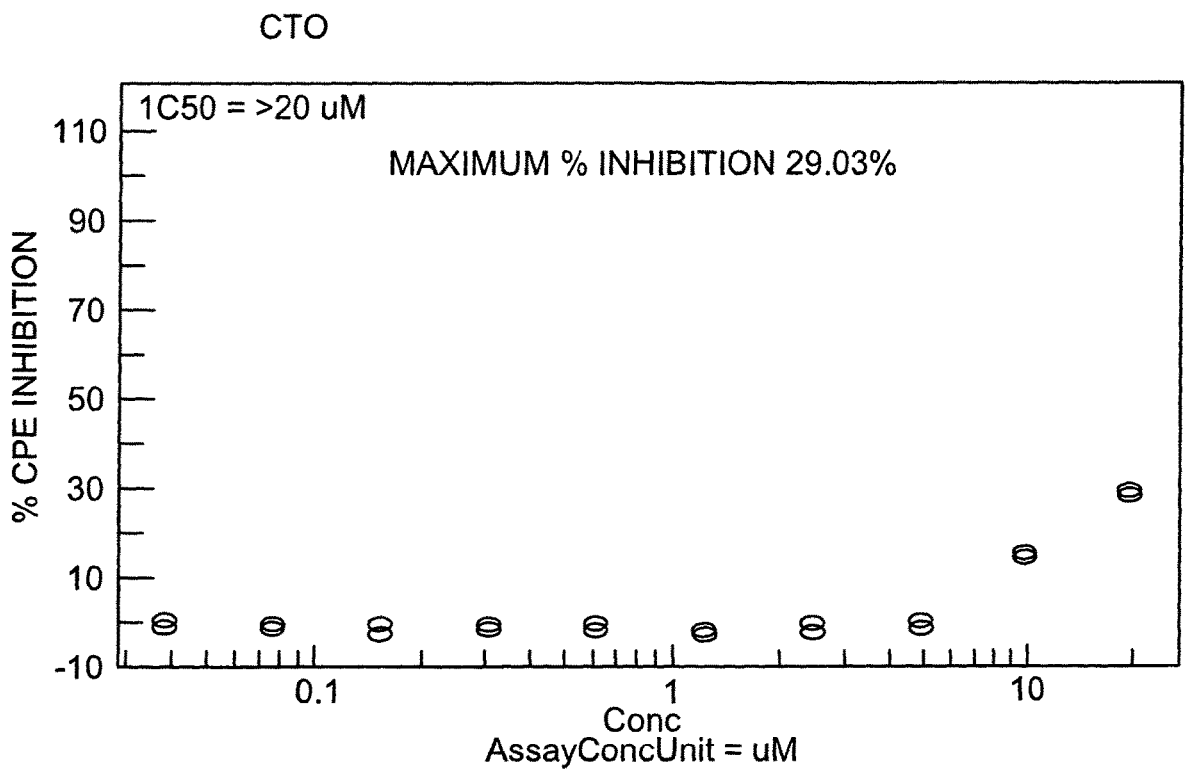

FIG. 2 illustrates the results of CTO treatment on the cytopathic effect-commonly referred to as "CPE" for SARS-CoV-2. The IC50 for CTO was >20 μM. Maximum % Inhibition was 29.03% recorded <20 μM concentration.

5. DETAILED DESCRIPTION OF THE INVENTION

The invention is achieved by evaluating the critical role of calcium in the expression and virulence of SARS-CoV-2 at every inflection point and targeting it, starting from infection, entry into the host cells, replication, and propagation to progression of disease in the life cycle of the virus. The strategy involves targeting the host-related antiviral effects and controlling the excessive adaptive responses (maladaptive immunity) to the virus by immune cells of the host and preventing the virus spread to other tissues and organs. CTO has unique effects on modulating the calcium signaling and the strategy is to use CTO to target SARS-CoV-2 and its variants at different inflection points in its life cycle.

SARS-CoV-2/COVID-19 Pandemic.

Two variants of SARS-CoV-2 have been discovered the G614 original variant and the D614G variant that has become the most prevalent form in the global pandemic.

Epidemiological studies indicate people who are at higher risk of severe illness from COVID-19 include individuals over 60 years of age with weaker immune systems, and patients with serious chronic medical conditions such as lung disease, diabetes, obesity, heart disease or cancer. COVID-19 can also occur in children, whose symptoms seem milder and may involve multisystem inflammatory syndrome. COVID-19 spreads via human-to-human transmission, mainly through respiratory droplets and close-quarter contact. However, SARS-CoV-2 has also been detected in detected in lungs, eyes, liver, kidney, brain/CNS, gastrointestinal tract, blood, saliva, urine and semen samples.

Within the context of the invention samples suspected of containing the virus include biological material samples, for example blood, serum, urine, cerebrospinal fluid, tears, nasal drip, sputum, saliva, tissue samples and the like. If desired, the anti-virus activity of a compound of the invention can be measured after application of the composition by observation and by methods including direct and indirect methods of detecting such activity. Quantitative, qualitative and semi-quantitative methods of determining such activity are all contemplated. The antiviral activity of a compound of the invention can be measured using standard screening protocols that are known. For example, the antiviral activity of a compound can be measured using the following methods: a) Cell-based SARS-CoV-2 virus immunodetection assay, b) Cell based SARS-CoV-2 virus cytopathic effect assay and c) Antiviral activity in a mouse model of SARS-CoV-2 infection Three clinical phenotypes of COVID-19 have been observed based on infection's progression: (i) mild, in patients with minor and nonspecific symptoms who do not progress to a more severe disease, (ii) moderate, with pneumonia or without hypoxia and localized inflammation in patients requiring hospitalization, and (iii) severe, with systemic hyperinflammation and acute respiratory distress syndrome (ARDS) in patients who require critical care management and are at risk of death. The incubation period of SARS-CoV-2 is about 14 days, with a median time of 4 to 5 days from exposure to symptom onset, and a median five days (range three to six days) for IgM detection with COVID-19. Virus has been detected for up to 21 days.

Understanding the life cycle and time course of SARS-CoV-2 from initial infection to excessive or maladaptive immune response leading to severe COVID-19 disease to death provides inflection points for therapeutic intervention. Development of vaccines against specific variants and antibodies that bind and neutralize the circulating virus may be used to prevent infection or prevent viral replication. Direct acting antivirals that bind to viral proteins to inhibit function and prevent viral replication and spread early in infection may be used but these drugs need to be tailored to the virus structure, for example remdesivir.

Host-directed antiviral drugs exploit different inflection points in the life cycle of the virus, for example during cell entry at the ACE2 receptor, during viral replication and viral protein phosphorylation and preventing the excessive production of cytokines by the adaptive immunity (or maladaptive immunity) of host responses and subsequent spread systemically. These provide a variety of druggable targets and understanding of the mechanisms is at an early stage for SARS-Co-V2.

The calcium signal has been shown to trigger the virulence of pathogens and to switch the infection from an acute to chronic stage (Broder et al, Nature Microbiology 2: 16184, 2016). For example, the Dengue virus and the West Nile virus disturb calcium homeostasis to favor viral replication cycle, and cells treated with calcium chelators and channel blockers suppress the production of viral yields (Balasubramanyam, et al EMJ Diabet. 2020; DOI: 10.33590/emjdiab/200608. Rotavirus infection activates the endoplasmic reticulum and store-operated calcium entry to promote viral replication (Chang-Graham et al, Science Reports 9: 10822, 2019). The influenza A virus induces calcium oscillations of host cells and the infection is markedly attenuated by chelation of both intracellular and extracellular calcium (Fujioka et al, Cell Host Microbe, 23: 809-818, 2018). Many viral proteins, known as viroporins, favor viral replication by enhancing the movement of ions and small molecules through membranes. Knockdown of the L-type $Ca^{2+}$ voltage-gated channel subunit inhibits porcine delta coronavirus. Both SARS-CoV and MERS-CoV possess ion channel activity (Bai et al, Nature Microbiology 2: 16184, 2016).

Recently the mechanism of infection by SARS-CoV-2 was reported to involve phosphorylation as a primary host response. Several viral proteins were detected, and one was to promote kinase activity and p38/MAP and cytokine production (Bouhaddou M et al, 2020, Cell doi:https://doi.org/10.1016.2020.06.034.

This invention contemplates inhibiting the phosphorylation of viral proteins of SARS-CoV-2 and variants and subsequent cytokine production by using CTO to inhibit calcium signaling that is required for phosphorylation of SARS-CoV-2 proteins and production of cytokines.

Cytokines are central to the pathophysiology of COVID-19 and have received the most attention in developing therapeutic products to treat progressive symptoms of COVID-19. Elevated levels of cytokines that appear detrimental to the host are reported, e.g., IL-1β, IL-1Ra, IL-6, IL-1β, VEGF, GM-CSF, INF-γ, IL-2, IL-8, MIP1-α, IL-1β, IL-6-sIL-6R-JAK-STAT3, monocyte chemoattractant protein-1 (MCP-1), IL-8 and TNF-α, particularly in the context of cytokine release syndrome (CRS) and the so-called 'cytokine storm' involving membrane permeability and inflammation. Numerous clinical trials are ongoing including anti-cytokine therapies, i.e., IL-6 and IL-R antagonists, interleukin-1, interleukin-6, anti-INF-γ and TNF inhibitors, as well as less targeted therapies, such as corticosteroids, chloroquine, or JAK inhibitors. However, there are some concerns regarding the use of IL-6 or IL-6R blockade or TNF-α inhibitors alone (Moore and June, Science 368: 473-4, 2020 2020).

The present invention provides a pharmaceutical composition of CTO comprising an effective amount of CTO to prevent or inhibit excessive production of several cytokines to dampen the maladaptive immune response and treat the cytokine storm, administered daily in the range of 50 mg/m2 to 1500 mg/m2 based on the patient's body surface. The present invention also provides a pharmaceutical composition of CTO comprising an effective amount of CTO to prevent and inhibit multisystem inflammatory syndrome in children under the age of ten years, using and effective amount of CTO.

Mode of Action of CTO

CTO is a small molecule with favorable pharmacokinetic and toxicokinetic profiles with multiple signaling targets associated with signal transduction pathways in cancer. CTO is a first-in-class inhibitor of non-voltage-gated calcium signaling. Calcium is a common control denominator in most physiological and pathological processes. (Kohn et al Proc Natl Acad Sci USA 92: 1307-11, 1995).

Calcium is maintained in the intracellular and extracellular milieu with the existence of a concentration gradient which is modulated according to cell demand, and is controlled by a series of channels, transporters and pumps. CAI (in CTO) acts on the membrane channel, the endoplasmic reticulum and mitochondria to control the extracellular and intracellular calcium gradient.

Efforts to find effective treatments for pathogenic viruses have focused on viral proteins termed viroporins, encoded by a range of viruses of clinical interest such as coronaviruses, hepatitis C virus, HIV-1, influenza A virus and picornaviruses. Viroporins participate in different steps of the viral cycle, such as increase in membrane permeability, cell entry, genome replication and release from infected cells by altering the calcium concentration in extracellular and intracellular stores, such as the endoplasmic reticulum and the mitochondria.

Calcium is an important regulator of many cellular enzymes and processes and an increase in calcium has detrimental effects for many cellular and viral functions. It has been suggested that alterations in calcium after infection with most animal viruses modulate several viral functions and play a part in host cell death. In studies with human T-cells, carboxyamidotriazole (CM base) modulated the calcium influx and the HIV LTR transcription dependent on it (Yasui et al J Biol Chem 272: 28762, 1997). The present invention provides the method using CTO to inhibit calcium signaling we expect is to inhibit the activity of viroporins and viral functions to make a significant impact in the treatment of COVID-19 patients. In chronic and infectious disease, aberrant calcium leads to production of multiple cytokines and inflammatory factors very similar to the several cytokines (about 10 different types) reported to be present in high levels in the blood of COVID-19 patients. These multiple cytokines contribute to respiratory failure, fever, circulatory, myocardial, and neurological damage observed in COVID-19 patients. The present invention provides the method and pharmaceutical compositions of the active ingredients of compound of this invention, CTO, a non-voltage-gated calcium signaling inhibitor, to inhibit multiple cytokines found increased in COVID-19 patients and to inhibit the viral replication in multiple systems as exemplified below. References cited herein all incorporated in their entireties.

Pharmaceutical Formulations

The compound of the invention is formulated with conventional carriers and excipients, which will be selected in accord with ordinary practice. All formulations will optionally contain excipients such as those set forth in the Handbook of Pharmaceutical Excipients (1986). While it is possible for the active ingredients to be administered alone it may be preferable to present them as pharmaceutical formulations. The formulations, both for veterinary and for human use, of the invention comprise the active ingredient and optionally together with one more acceptable carriers thereof and optionally other therapeutic ingredients. The carrier(s) must be acceptable in the sense of being compatible with the other ingredients of the formulation and physiologically innocuous to the recipient thereof.

The compound of the invention is formulated in aqueous form for pediatric use and for application by tubing, e.g., nasogastric application using available clinical compounding suspending vehicles, e.g., Ora-Plus among others.

Formulations of the present invention suitable for oral administration may be presented as discrete units such as capsules, cachets or tablets each containing a predetermined amount of the active ingredient as a powder, as a solution or a suspension in an aqueous or non-aqueous liquid; or as an oil-in-water liquid emulsion or a water-in-oil-liquid emulsion.

For infections of the eye or other external tissues, e.g., mouth and skin, the formulations are preferably applied as a topical ointment or cream containing the active ingredient in an amount of 0.075 to 20% w/w. Formulations suitable for topical administration in the mouth include lozenges comprising the active ingredient in a flavored basis usually sucrose and acacia; pastilles comprising the active ingredient in the inert basis such as gelatin and glycerin or sucrose and acacia. Formulations for rectal administration may be presented as a suppository with a suitable base comprising for example cocoa butter or a salicylate. Formulations suitable for intrapulmonary or nasal administration may be prepared according to conventional methods and may be delivered with other therapeutic agents. Formulations suitable for vaginal administration may be presented as pessaries, creams, gels, or spray formulations containing in addition to the active ingredient CTO such carriers as are known in the art to be appropriate.

Effective dose of CTO depends at least on the nature of the condition being treated, whether the compound is being used prophylactically or against an active viral infection, the method of delivery, and the pharmaceutical formulation, and will be determined by the physician using conventional dose escalation studies. It can be expected to be from about 50 mg/m2/day to about 1500 mg/m2/day. For example, for daily fixed dose for an adult human with about a BSA (Body Surface Area) of 1.8 to about BSA of 2.2, the dose will range from 100 mg to 800 mg, preferably between 200 mg and 600 mg and may be taken as a single or multiple dose.

Routes of Administration

One or more compounds of the invention (herein referred to as the active ingredients) are administered by any route appropriate to the condition to be treated. Suitable routes include oral, nasogastric tube, rectal, nasal, topical (including buccal and sublingual), vaginal and parenteral (including subcutaneous, intramuscular, intravenous, intradermal, intrathecal and epidural) and the like. It will be appreciated that the preferred route may vary with the condition of the recipient. An advantage of the compounds of this invention is that they are orally bioavailable and can be dosed orally.

Combination Therapy

Combination of CTO with other therapeutic drugs are typically selected based on the condition to be treated, cross-reactivities of ingredients and pharmacological properties of the combination. For example, when treating an infection, e.g., SARS-COV-2, the compositions of the invention are combined with other active therapeutic agents used in the standard of care clinically setting. Preferably, the other active ingredients or drugs used in stand or care in clinics are interferons, azithromycin, chloroquine, hydroxychloroquine, dexamethasone, remdesivir, lopinavir, ritonavir, antagonists of the renin-angiotensin system, anti-inflammatory agents, anti-coagulation agents or other antiviral agents or mixtures thereof.

In another embodiment the present invention discloses pharmaceutical compositions comprising a compound of the present invention in combination with any agent having a therapeutic effect when used in combination with the compound of the present invention and a pharmaceutically acceptable carrier or excipient.

It is also possible to combine the compound of the present invention with one or more other active therapeutic agents in a unitary dosage form for simultaneous or sequential administration to a patient. The combination therapy may be administered as a sequential or simultaneous regimen. When administered sequentially, the combination may be administered in two or more administrations. The combination therapy may provide "synergistic" effects, i.e., the effect achieved when the active ingredients used together is greater than the sum of the effects that results from using the compounds separately.

The present invention provides the method and pharmaceutical compositions of the active ingredients of compound of this invention, CTO, a non-voltage-gated calcium signaling inhibitor, to inhibit multiple cytokines found increased in COVID-19 patients and to inhibit the viral replication and propagation of SARS-CoV-2 and variants in multiple systems as exemplified below. The references cited herein are incorporated in their entirety herein.

EXAMPLE 1

In a Phase I trial of CTO testing the safety and tolerability of CTO in cancer patients, Plasa samples were obtained from three patients after administration of different doses of CTO daily as follows: 1) NSCLC Patient 002-46 (CTO 555 mg/m2), 2) NSCLC Patient 002-50 (CTO 427 mg/m2) and 3) Ovarian Cancer Patient 002-53 (CTO 427 mg/m2) The levels of cytokines were measured by using the HCYT-MAG-60K-PX30/Milliplex MAP Human Cytokine/Chemokine Magnetic Bead Panel from Milliplex, USA.

Results obtained indicated that administration of CTO at doses ranging from 427 mg/m2 to 555 mg/m2 resulted in a reduction in levels of several cytokines including VEGF, GM-CSF, INF-γ, IL-2, IL-12p70, IL-13, IL-15, IL-17a, IL-1RA, IL-1α, IL-2, IL1-4, IL-6, IL-8, il-10, MIP1-α. IL-1 TNF-α.

In contrast the administration of CTO at doses ranging from 427 mg/m2 to 555 mg/m2 resulted in an increase of levels of following cytokines including, EGF, IFN α2, IL-1β, IL-12p40 as shown in Table 1. Both IFN α2 and IL-10 have anti-inflammatory activity. These results are highly unexpected because CTO reduced the levels of the pro-inflammatory cytokines while also increased the levels of the some cytokines like with anti-inflammatory activity, for example IFNα2 and IL-10.

Table 1. Target Cytokines in Luminex Panel Testing of Plasma Specimens-Results

Expressed as Cytokine (+ increased) or (− decreased)
VEGF—(−)
EGF—(+)
G-CSF
GM-CSF—(−)
IFNα2—(—I—)
IFNγ—(−)
IL-1β—(+)
IL-12p40—(+)
IL-12p70—(−)
IL-13—(−)
IL-15—(−)
IL-17A—(−)
IL-1RA—(−)
IL-1α
IL-2—(−)
IL-4—(−)
IL-6—(−)
IL-8—(−)
IP-10—(−)
MIP1a—(−)
RANTES—(+)
**IL-1β—(−)
**TNFα—(−)

EXAMPLE 2

In the present invention, a patient infected with SARS-CoV-2 exhibited common symptoms including cough, chest pain, joint pain, fatigue, fever, myalgia, joint pain, chest pain, neurological confusion, rhinitis, red eyes, headache, vertigo, fatigue, gastrointestinal symptoms of diarrhea and blood in stools. The patient was unaware of being infected and did not seek medical care. Within 14 days the patient lost twelve pounds in weight. The patient obtained a supply of CTO capsules of 200 mg dose. The patient took 600 mg dose daily on a three-hour fasting regimen (2 hr before and 1 hour after dosing). On the second day the patient felt a great improvement in most of the symptoms and remained at constant weight. After three days at 600 mg/day daily, the dose was reduced to 400 mg/day for the next four days, and to 200 mg daily for the next fourteen days. All this time, the patient continued to go to work as an essential worker. The patient was found positive for antibodies to SARS-CoV-2 and continued to show some symptoms (fatigue, joint pain, chest pain) even after several weeks.

EXAMPLE 3

Also, in the present invention, the effect of CTO on SARS-CoV-2 was tested using the CPE assay using Vero E6 cells. Cell viability was measured using Promega Cell Titer Glo. The assay was optimized for performance as measured by 85%-95% CPE 72 hours post-inoculation of host cells and Z'>0.5 (cell viability of virus infected cells vs non-infected cells). Calpain inhibitor IV, Chloroquine, Aloxistatin, hydroxychloroquire and remdesvir were tested at 10 concentrations in parallel as reference compounds. Results obtained showed that the IC50 for CTO was >2004 CTO (the highest dose tested). The Maximum % inhibition recorded was 29.03%. In the non-infected Vero E6 cells the EC 50 for CTO was 14.87 µM. Treatment with CTO inhibited replication of SARS-CoV-2 up to 5 µM and cell viability remained above 90%. The results obtained are similar to those obtained when Vero E6 cells were pretreated with pegylated interferon alpha (Ogando N S, et al, SARS-coronavirus-2 replication in Vero E6 cells: replication kinetics, rapid adaptation and cytopathology, bioRxiv preprint doi: https://doi.org/10.1101/2020.04.20.049924, April 2020). The results obtained indicate that CTO treatment of the Vero E6 cells modified them and made them less susceptible to SARS-CoV-2 attack and infection. FIG. 2. These results suggest host-directed antiviral effects of CTO against SARS-CoV-2.

The present invention is not to be limited in scope by the embodiment disclosed in the example which is intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Those skilled in the art will recognize or be able to ascertain using no more than routine experimentation, any equivalents to the specific embodiments of the invention described herein. Such equivalents are intended to be encompassed by the claims.

What is claimed is:

1. A method for inhibiting the virulence and expression of SARS-CoV-2 in a human patient having a mild stage of COVID-19, comprising administering the pharmaceutical composition comprising carboxyamidotriazole orotate for treating SARS-CoV-2 infection and a phenotype of COVID-19 disease in a human patient, wherein the effective amount, formulation type and route of the administration of the pharmaceutical composition are determined as appropriate to the condition of the human patient having a mild stage of COVID-19 to inhibit entry, phosphorylation, replication and propagation of SARS-CoV-2, wherein the effective amount is a once daily dose of carboxyamidotriazole orotate in the range of 50 mg/m² to 1500 mg/m² based on the body surface of the human patient.

2. A method for inhibiting the production of cytokines with inflammatory activity in a human patient having a moderate stage of COVID-19, comprising administering the pharmaceutical composition comprising carboxyamidotriazole orotate for treating SARS-CoV-2 infection and a phenotype of COVID-19 disease in a human patient, wherein the effective amount, formulation type and route of the administration of the pharmaceutical composition are determined as appropriate to the condition of the human patient having a moderate stage of COVID-19 to inhibit the production of cytokines with inflammatory activity in the human patient, wherein the effective amount is a once daily dose of carboxyamidotriazole orotate in the range of 50 mg/m² to 1500 mg/m² based on the body surface of the human patient, and wherein said cytokines comprise VEGF, GM-CSF, INF-γ, IL-2, IL-12p70, IL-13, IL-15, IL-17a, IL-1RA, IL-1α, IL-2, IL1-4, IL-6, IL-8, IL-10, MIP1-α, IL-1β and TNF-α.

3. A method of treating a human patient having a moderate stage of COVID-19, comprising administering the pharmaceutical composition comprising carboxyamidotriazole orotate for treating SARS-CoV-2 infection and a phenotype of COVID-19 disease in a human patient, wherein the effective amount, formulation type and route of the administration of the pharmaceutical composition are determined as appropriate to the condition of the human patient having a moderate stage of COVID-19 to increase production of interferon-2a with antiviral activity and IL-10 with anti-inflammatory activity, wherein the effective amount is a once daily dose of carboxyamidotriazole orotate in the range of 50 mg/m² to 1500 mg/m² based on the body surface of the human patient.

4. A method of treating a human patient having a severe stage of COVID-19, comprising administering the pharmaceutical composition comprising carboxyamidotriazole orotate for treating SARS-CoV-2 infection and a phenotype of COVID-19 disease in a human patient, wherein the effective amount, formulation type and route of the administration of the pharmaceutical composition are determined as appropriate to the condition of the human patient having a severe stage of COVID-19 to inhibit production of cytokines, inhibit hyperinflammation, inhibit coagulation, and inhibit damage to organs including heart, liver, kidneys, brain and lungs, wherein the effective amount is a once daily dose of carboxyamidotriazole orotate in the range of 50 mg/m² to 1500 mg/m² based on the body surface of the human patient.

5. The method according to claim 1, wherein a patient with the mild stage of the COVID-19 is further treated with a standard of care drug.

6. The method according to claim 2, wherein a patient with the moderate stage of the COVID-19 is further treated with a standard of care drug.

7. The method according to claim 3, wherein a patient with the moderate stage of the COVID-19 is further treated with a standard of care drug.

8. The method according to claim 4, wherein a patient with the severe stage of the COVID-19 is further treated with a standard of care drug.

* * * * *